US007084263B2

(12) United States Patent
Dobbins et al.

(10) Patent No.: US 7,084,263 B2
(45) Date of Patent: Aug. 1, 2006

(54) PROCESS FOR ISOLATING GENISTIN FROM MIXTURES OF SOY ISOFLAVONES

(75) Inventors: Thomas A. Dobbins, Howard, OH (US); Deborah C. Hurst, New Concord, OH (US)

(73) Assignee: Wiley Organics, Inc., Coshocton, OH (US)

( * ) Notice: Subject to any disclaimer, the term of this patent is extended or adjusted under 35 U.S.C. 154(b) by 0 days.

(21) Appl. No.: 10/397,692

(22) Filed: Mar. 26, 2003

(65) Prior Publication Data

US 2003/0216557 A1 Nov. 20, 2003

Related U.S. Application Data

(60) Provisional application No. 60/367,566, filed on Mar. 26, 2002.

(51) Int. Cl.
*C07H 17/00* (2006.01)
*A23J 1/14* (2006.01)

(52) U.S. Cl. .......................... 536/8; 536/128; 424/757; 514/2; 514/456; 426/634; 426/46; 530/378; 435/68.1

(58) Field of Classification Search .................... 536/8, 536/128; 424/757; 426/634, 46; 530/378; 435/68.1; 514/2, 456
See application file for complete search history.

(56) References Cited

U.S. PATENT DOCUMENTS

| | | | | |
|---|---|---|---|---|
| 4,428,876 A | | 1/1984 | Iwamura | |
| 4,594,412 A | | 6/1986 | Kitagawa | |
| 5,851,792 A | * | 12/1998 | Shen et al. | 435/68.1 |
| 5,919,921 A | | 7/1999 | Waggle et al. | |
| 5,932,221 A | * | 8/1999 | Day | 424/757 |
| 6,033,714 A | | 3/2000 | Gugger et al. | |
| 6,228,993 B1 | | 5/2001 | Konwinski | |
| 6,369,200 B1 | | 6/2001 | Dobbins et al. | |
| 6,261,565 B1 | | 7/2001 | Empie et al. | |
| 6,355,816 B1 | | 3/2002 | Dobbins | |
| 6,410,699 B1 | | 6/2002 | Takebe et al. | |

FOREIGN PATENT DOCUMENTS

| | | |
|---|---|---|
| EP | 0795553 | 9/1997 |
| WO | 99/34810 | 7/1999 |

OTHER PUBLICATIONS

P.A. Ireland et al., "Saponins Content of Soya and Some Commercial Soya Products by Means of High-performance Liquid Chromatography of the Sapogenins," *J. Sci. Food Agric.*, pp. 694-698 (1986).
K. Hostettmann et al., "Saponins, Chemistry and Pharmacology of Natural Products," *Cambridge University Press*, pp. 142-145.

* cited by examiner

*Primary Examiner*—Shaojia Anna Jiang
*Assistant Examiner*—Devesh Khare
(74) *Attorney, Agent, or Firm*—Thompson Hine LLP

(57) ABSTRACT

A process for enriching the relative concentration of genistin from a mixture of isoflavones is described. In accordance with one aspect of the invention, the process comprises providing a material containing a mixture of isoflavones, extracting the material with an aqueous organic solvent solution, adding calcium oxide or calcium hydroxide to the extract to form calcium-isoflavone complexes and separating precipitated calcium-isoflavone complexes from the extract. The precipitated calcium-isoflavone complexes contain a higher concentration of genistin complexes than daidzin and glycitin complexes.

22 Claims, No Drawings

PROCESS FOR ISOLATING GENISTIN FROM MIXTURES OF SOY ISOFLAVONES

CROSS REFERENCE TO RELATED APPLICATION

This application claims priority from U.S. Provisional Application Ser. No. 60/367,566, filed Mar. 26, 2002.

BACKGROUND OF THE INVENTION

Isoflavones are a unique class of phytoestrogens—plant hormones—that naturally occur in many plants, including soybeans (Glycine max). The three isoflavones found in soybeans are genistin, daidzin, and glycitin, typically in a ratio of genistin: daidzin: glycitin of 1.1:1.0:0.3.

It is widely anticipated that market demand for soy isoflavones will continue to grow. Scientists have demonstrated that isoflavones have the ability to inhibit cancer cell growth, and some researchers believe that isoflavones may contribute to soy's ability to lower blood-cholesterol levels.

Research shows that soy isoflavones have a wide range of health benefits that include moderating normal symptoms associated with menopause and promoting bone and heart health. It appears that about 100 milligrams of isoflavones (expressed in the glycoside form) are necessary to deliver most of these health benefits. This is about the average amount consumed daily by Asians, who have a much lower incidence of heart disease, osteoporosis, and uncomfortable menopausal symptoms compared to Western societies.

Some women's health problems during and after middle age are related to a changing hormonal state. Consuming soy isoflavones can help moderate the natural hormonal changes associated with several menopausal and postmenopausal symptoms.

Soy isoflavones are potent anti-oxidants capable of reducing the amount of LDL-cholesterol (bad cholesterol) that undergoes modification in the body. Entry of the modified LDL-cholesterol into the walls of blood vessels contributes to the formation of plaques. These plaques cause the blood vessels to lose their ability to function normally. Research in both animals and humans shows that ingesting soy isoflavones can help maintain normal blood vessel function Soy isoflavones are actively studied for their effects on maintaining and improving bone health. Women can lose up to 15% of their total bone mass in the early years following the onset of menopause. This loss can be quite detrimental, particularly to women who enter menopause with weaker bones. Emerging research shows that isoflavones appear to play a role in both preventing bone loss and increasing bone density.

A body of research suggests that the most pharmacologically active soy isoflavone is genistin. Therefore, a method of separating genistin from daidzin and glycitin or of enriching the proportion of genistin in soy isoflavone concentrates is desirable.

The isoflavones found in soybeans occur predominantly as glucones or glycosides (with sugars), with only a minor aglucones or aglycons (without sugars) content. The glucones have the glucose molecule attached, and include genistin, daidzin and glycitin. The aglucones are isoflavones without the glucose molecule, and they include genistein, daidzein and glycitein. In addition, an appreciable percentage of the glucones occur as malonates or acetates. The malonyl and acetyl moieties of soy isoflavones glucones are thermally labile, particularly at elevated pH (from about 9.5 to 11.0) and can be easily converted to the corresponding simple glucones by digestion at moderate temperatures with sodium or potassium hydroxide.

Traditionally, the separation of genistin from daidzin and glycitin has required laborious ultrafiltration followed by preparative chromatography (see, e.g., U.S. Pat. No. 5,679,806) or ion-exchange resins (see, e.g., U.S. Pat. No. 6,020,471) of large volumes of solutions due to the modest solubility of soy isoflavones. These processes employ various resins to adsorb the isoflavones from aqueous solutions heated to various temperatures to take advantage of the temperature-sensitive differential solubilities of isoflavones in order to effect their separation (see, e.g., U.S. Pat. No. 5,702,752).

SUMMARY OF THE INVENTION

The process described herein takes advantage of the discovery that the readily synthesized calcium complex of genistin is markedly less soluble in suitable mixtures of polar organic solvents (e.g., acetone, methanol, ethanol) and water than the corresponding calcium complexes of daidzin and glycitin, permitting the genistin to be readily separated by filtration or centrifugation.

In accordance with one aspect of the present invention a soy isoflavone concentrate is slurried with a solvent mixture of acetone and water. The weight ratio of acetone to water typically runs from about 3:1 to 5:1 with a ratio of about 4:1 being preferred in most instances. The slurry is reacted with a stoichiometric excess of calcium hydroxide or calcium oxide to form the genistin complex. Typically about a 2- to 4-fold excess is used. The calcium complex of genistin is recovered and then reconverted to genistin by reaction with a mineral acid. In accordance with one embodiment of the invention, the mineral acid is HCl. Although other mineral acids are also useful, HCl is preferred because the reaction yields calcium chloride, which is soluble in the HCl and facilitates collection and recovery of the genistin. To enhance the purity of the recovered genistin, the liming and recovery process can be repeated as illustrated in the following examples. To further purify the product, the product can be recrystallized from a mixture of ethanol and water.

The invention can also be used to prepare the corresponding aglucone genistein by converting the recovered genistin to genistein.

DETAILED DESCRIPTION OF THE INVENTION

All documents cited are, in relevant part, incorporated herein by reference; the citation of any document is not to be construed as an admission that it is prior art with respect to the present invention.

The present invention is directed to a process for enriching the relative concentration of genistin from a mixture of isoflavones. In accordance with one aspect of the invention, the process comprises providing a material containing a mixture of isoflavones, extracting the material with an aqueous organic solvent solution, adding calcium oxide or calcium hydroxide to the extract to form calcium-isoflavone complexes and separating precipitated calcium-isoflavone complexes from the extract. The precipitated calcium-isoflavone complexes contain a higher concentration of genistin complexes than daidzin and glycitin complexes. The latter complexes are believed to be more soluble in the aqueous organic solvent extraction solution.

In accordance with another aspect of the invention, a process for enriching the proportion of genistin in soy isoflavone concentrates is described. This process comprises extracting a soy isoflavone concentrate with an aqueous organic solvent solution, contacting the extract with calcium oxide or calcium hydroxide thereby forming calcium-isoflavone complexes, which precipitate from the extract solution, and removing the precipitated calcium-isoflavone complexes. The recovered precipitated calcium-isoflavone complexes contain an enriched concentration of calcium-genistin complexes. In accordance with certain aspects of the present invention, the weight ratio of calciumgenistin complex to calcium-daidzin complex is at least about 20 times, preferably about 50 times and most preferably about 90 times, the initial weight ratio of genistin to daidzin present in the starting soy isoflavone concentrate.

In accordance with certain aspects of the present invention, the precipitated calcium-isoflavone complexes can be reconverted to free the isoflavones from the calcium complex and thereby form a slurry containing free isoflavone glycosides. The free isoflavone glycosides can be separated from the slurry by centrifugation, filtration, or settling and decanting. The product recovered comprises genistin enriched isoflavone glycosides of relatively high genistin content (i.e., total isoflavone content). The free isoflavone glycosides obtained can be further purified by repeating the extraction, liming, separation and reconverting steps.

The recovered product typically has a genistin content exceeding about 70%, preferably about 80% and most preferably 90%. The purity can be further increased by dissolving the recovered product in a suitable solvent, filtering and allowing the isoflavone glycosides to crystallize.

The corresponding aglucone, genistein, can be obtained by converting the recovered glycoside isoflavones to aglucone isoflavones using conventional techniques. For example, acidic or enzymatic hydrolysis can be used to cleave the 1,4-glucoside bonds. Methods for converting glycoside isoflavones to aglucone isoflavones are disclosed in U.S. Pat. Nos. 5,919,921; 5,827,682 and Japanese Patent Application 258,669 to Obata, et al.

The organic solvent solutions useful in the present invention include solutions containing a lower alcohol, a ketone or a combination thereof. Acetone is a particularly useful organic solvent. Examples of useful lower alcohols include methanol, ethanol and mixtures thereof. The solvent-to-water ratio for the extraction solution will typically range from about 3 to about 5 parts organic solvent to one part water and is optimally approximately 4:1 by weight. Organic solvent solutions outside these ranges may be useful, but the efficiency of the extraction may be reduced. A solvent solution containing 4 parts acetone and 1 part water is a particularly useful. The solvent solutions described herein are useful in the extraction step as well as in the purification step wherein the isoflavone glycosides are recovered by crystallization.

The ratio of isoflavone containing material or soy isoflavone concentrate to aqueous organic solvent solution can vary and is not particularly limited. The efficiency of the extraction using a ratio of isoflavone containing material to solvent solution of approximately 10 to 20 by weight is typically very high. However, ratios outside this range will also work although efficiencies may be reduced. Furthermore, the extraction may be repeated one or more times to increase efficiency.

The isoflavones are typically extracted at an elevated temperature. In accordance with one embodiment of the present invention, the isoflavones-containing material is digested in a mixture of acetone and water at or about the reflux temperature for acetone (56° C. at atmospheric pressure or higher temperatures at elevated pressures). In accordance with this embodiment, calcium oxide or calcium hydroxide is added to the extract solution at an elevated temperature of about 50° C. The temperature is maintained at about 40 to 45° C. for a time sufficient to form the calcium-isoflavone complex. The calcium-isoflavone complexes are separated from the extract by centrifugation, filtration, or settling and decanting while maintaining the extract solution at the elevated temperature. The precipitated material contains a mixture of unreacted lime and the calcium-isoflavone glycoside complex. The calcium-isoflavone glycoside complex comprises primarily the calcium complex of genistin; the corresponding complexes of daidzin and glycitin are more soluble and tend to stay in solution.

The recovered calcium-isoflavone glycoside complex can be reconverted to the free glycoside form. In accordance with one embodiment, the calcium-isoflavone glycoside complex is added to a solution of concentrated hydrochloric acid and water and heated to effect conversion of the complex to calcium chloride and free isoflavone glycosides. The free isoflavone glycosides then precipitate out of solution and can be recovered by filtration, centrifugation, etc.

To further purify the free isoflavone glycosides, they can be dissolved in an aqueous organic solvent solution and filtered at an elevated temperature to remove acid insolubles. The filtrate can then be reduced in volume by stripping off excess solvent at which point crystals of extremely pure genistin begin to form. The temperature of the solution can be reduced whereupon additional genistin crystallizes from solution and can be recovered.

The concentration of the genistin in the resulting product can be further increased by digesting a genistin-enriched composition in an aqueous organic solvent solution. In accordance with one embodiment, the solids are digested in 10 times their mass in a solution containing 80% ethanol and 20% water at reflux (79° C.) for 90 minutes. The extraction solution is then filtered at a temperature exceeding about 60° C. The resulting dried filter cake comprises a high concentration of genistin with very little daidzin (<1%, typically).

The present invention is illustrated in more detail by the following non-limiting examples. The examples are intended to be illustrative and should not be interpreted as limiting or otherwise restricting the scope of the invention in any way.

EXAMPLE 1

1.) 100 grams of commercial soy isoflavone concentrate ("Prevastein" from the Central Soya Corporation of Fort Wayne, Ind., with a composition of 49.71% total isoflavones, including 33.91% genistin, 13.04% daidzin, 0.69% glycitin glycosides; 1.26% genistein, 0.74% daidzein, 0.07% glycitein aglycons) was slurried with 1.5 liters of a solvent containing of 80% by weight acetone/20% by weight water. The mixture was heated to 50 degrees C. and 65 grams of calcium hydroxide was added over a period of 30 minutes with vigorous agitation. The color of the liquid phase immediately became a vivid lemon yellow, the characteristic hue of isoflavone solutions at an elevated pH.

2.) The mixture was stirred while maintaining a temperature of 40 to 45 degrees C. for 90 minutes, then filtered at this temperature through Whatman #4 paper (20 microns) on a Buechner funnel. Filtration is extremely rapid, with no blinding. The filter cake consists of a mixture of unreacted lime (white) and the calcium-isoflavone glycoside complex (predominantly the calcium complex of genistin; the calcium complexes of daidzin and glycitin are far more soluble and tend to remain in solution). The calcium isoflavone 'salts' have a yellow color that resembles 'stadium mustard.' The filtrate is very clear, non-turbid, and lemon yellow in color. Very little additional material precipitates when the filtrate is cooled to 18 degrees C.

3.) The filter cake was added to a vigorously agitated mixture of 150 grams of concentrated HCl in 1,000 ml of water and heated to 40 degrees C. This temperature was maintained for three hours to effect the conversion of the calcium isoflavone complex to calcium chloride and free isoflavone glycosides. The yellow color disappears almost immediately upon acidification, and is replaced by a pale pink or rose color. When the reaction is complete the slurry has a pH of 2.0 to 2.5 and the suspended solids are off-white in color.

4.) The slurry was filtered at 40 degrees C. through Whatman #541 hardened filter paper on a Buechner funnel.

5.) In a second iteration of step #1 above, the filter cake was slurried in 1.5 liters of a solvent consisting of 80% by weight acetone/20% by weight water at 50 to 55 degrees C. 50 grams of calcium hydroxide was added over a period of 30 minutes with vigorous agitation. The color of the liquid phase immediately became a vivid lemon yellow and the calcium-isoflavone complex (once again predominantly the calcium complex of genistin) fell out of solution.

6.) In a second iteration of step #2 above, once again the mixture was stirred while maintaining a temperature of 40 to 45 degrees C. for 90 minutes, then filtered at this temperature through Whatman #4 paper (20 microns) on a Buechner funnel. Filtration is extremely rapid, with no blinding. Once again, the filter cake consists of a mixture of unreacted lime (white) and the calcium-isoflavone glycoside complex, which has a muddy yellow color that resembles 'stadium mustard.' The filtrate was a very clear, non-turbid, lemon yellow.

7.) In a second iteration of step #3 above, the filter cake was added to a vigorously agitated mixture of 150 grams of concentrated HCl in 1,000 ml of water and heated to 40 degrees C. This temperature was maintained for three hours to effect the conversion of the calcium-isoflavone complex to calcium chloride and free isoflavone glycosides. The yellow color disappeared almost immediately, replaced by a pale pink or rose color. When the reaction is complete the slurry has a pH of 2.0 to 2.5 and the suspended solids are off-white in color.

8.) In a second iteration of step #4 above, the slurry was filtered at 40 degrees C. through Whatman #541 filter paper on a Buechner funnel. The filter cake was dissolved in 3.5 liters of a solvent consisting of 80% by weight acetone/20% by weight water. This solution was filtered hot through Whatman #4 paper to remove acid-insoluble particles arising from the lime, presumably silicaceous compounds.

9.) The filtrate from the preceding step was reduced in volume to 1.3 liters by stripping off acetone at ambient pressure. Crystals of extremely pure genistin began to form once the volume was reduced below 2.5 liters, even at 56 degrees C. The mixture was allowed to cool to 30 to 32 degrees C. with very gentle agitation, then filtered through Whatman #4 paper (20 microns) on a Buechner funnel. The filter cake was washed with cold (5 degrees C.) acetone and dried in vacuo at 80 degrees C. to give glistening, ivory-colored crystalline plates with a composition of 97.35% genistin, 2.64% daidzin, no detectable glycitin or isoflavone aglycons. Recovery: 17.4 grams of 33.9 grams of the genistin contained in the starting material (65%).

Note: If only a single liming and subsequent acidification are performed, the resulting material has an overall purity (i.e. total isoflavone content) of 92.56%, having a composition of 89.38% genistin, 2.95% daidzin, and 0.14% glycitin.

10.) Once the genistin content exceeds 96% and the level of residual daidzin is less than 3%, the solids can be digested in 10 times their mass of a solvent containing 80% by weight water and 20% by weight ethanol at reflux (79 degrees C.) for 90 minutes, then filtered through Whatman #4 filter paper at a temperature exceeding 60 degrees C. The dried filter cake consists of 99.0+% genistin, <1.0% daidzin. The recovery of genistin in this step exceeds 94%.

EXAMPLE 2

1.) 100 grams of a soy isoflavone concentrate with the following composition: 74.48% total isoflavones, 60.72% genistin, 13.16% daidzin, 0.60% glycitin glycosides; 0.24% genistein, 0.22% daidzein, 0.01% glycitein aglycons, was slurried with 1.5 liters of a solvent consisting of 80% by wt. acetone/20% by wt. water. The mixture was heated to 50 degrees C. and 65 grams of calcium hydroxide was added over a period of 30 minutes with vigorous agitation. The color of the liquid phase immediately became a vivid lemon yellow, the characteristic hue of isoflavone solutions at elevated pH (i.e. 10+).

2.) The mixture was stirred while maintaining a temperature of 40 to 45 degrees C. for 90 minutes, then filtered at this temperature through Whatman #4 paper (20 microns) on a Buechner funnel. Filtration is extremely rapid, with no blinding. The filter cake consists of a mixture of unreacted lime (white) and the calcium-isoflavone glycoside complex (predominantly the calcium complex of genistin; the calcium complexes of daidzin and glycitin are far more soluble and tend to remain in solution. The calcium isoflavone 'salts' have a yellow color that resembles 'stadium mustard.' The filtrate is very clear, non-turbid, and lemon yellow in color. Very little additional material precipitates when the filtrate is cooled to 18 degrees C.

3.) The filter cake was added to a vigorously agitated mixture of 150 grams of concentrated HCl in 1,000 ml of water and heated to 40 degrees C. This temperature was maintained for three hours to effect the conversion of the calcium isoflavone complex to calcium chloride and free isoflavone glycosides. The yellow color disappears almost immediately upon acidification, and is replaced by a pale pink or rose color. When the reaction is complete the slurry has a pH of 2.0 to 2.5 and the suspended solids are off-white in color.

4.) The slurry was filtered at 40 degrees C. through Whatman #541 hardened filter paper on a Buechner funnel.

5.) The filter cake was slurried in 1.5 liters of a solvent consisting of 80% by weight acetone/20% by weight water at 50 to 55 degrees C. 50 grams of calcium hydroxide was added over a period of 30 minutes with vigorous agitation. The color of the liquid phase immediately became a vivid lemon yellow and the calcium-isoflavone complex (once again predominantly the calcium complex of genistin) fell out of solution.

6.) In this second iteration, once again the mixture was stirred while maintaining a temperature of 40 to 45 degrees C. for 90 minutes, then filtered at this temperature through Whatman #4 paper (20 microns) on a Buechner funnel. Filtration is extremely rapid, with no blinding. Once again, the filter cake consists of a mixture of unreacted lime (white) and the calcium-isoflavone glycoside complex, which has a muddy yellow color that resembles 'stadium mustard.' The filtrate was a very clear, non-turbid, lemon yellow.

7.) The filter cake was added to a vigorously agitated mixture of 150 grams of concentrated HCl in 1,000 ml of water and heated to 40 degrees C. This temperature was maintained for three hours to effect the conversion of the calcium-isoflavone complex to calcium chloride and free isoflavone glycosides. The yellow color disappeared almost immediately, replaced by a pale pink or rose color. When the reaction is complete the slurry has a pH of 2.0 to 2.5 and the suspended solids are off-white in color.

8.) The slurry was filtered at 40 degrees C. through Whatman #541 filter paper on a Buechner funnel. The filter cake was dissolved in 3.5 liters of a solvent consisting of 80% by weight acetone/20% by weight water. This solution was filtered hot through Whatman #4 paper to remove acid-insoluble particles arising from the lime, presumably silicaceous compounds.

9.) The filtrate from the preceding step was reduced in volume to 1.3 liters by stripping off acetone at ambient pressure. Crystals of extremely pure genistin begin to form once the volume is reduced below 2.5 liters, even at 56 degrees C. The mixture is allowed to cool to 25 to 30 degrees C. with very gentle agitation, then filtered at this temperature through Whatman #4 paper (20 microns) on a Buechner funnel. Filtration is extremely rapid, with no blinding. The filter cake is washed with cold (5 degrees C. acetone and dried in vacuo to 80 degrees C. to give glistening, ivory-colored crystalline plates of 99%+ genistin glycoside; recovery=65% of the genistin contained in the starting material.

Having described the invention in detail and by reference to specific embodiments thereof, it will be apparent that numerous modifications and variations are possible without departing from the scope of the invention defined by the following claims.

What is claimed is:

1. A process for enriching genistin from a mixture of isoflavones, comprising:

(a) providing a material containing a mixture of isoflavones;

(b) extracting said material with an aqueous organic solvent solution;

(c) adding calcium oxide or calcium hydroxide to the extract to form calcium-isoflavone complexes in the extract; and (d) separating precipitated calcium-isoflavone complexes from the extract.

2. The process of claim 1 wherein the organic solvent solution is a solution containing an alcohol of low molecular weight, a ketone or a combination thereof.

3. The process of claim 2 wherein the alcohol is selected from the group consisting of methanol, ethanol and mixtures thereof.

4. The process of claim 2 wherein the ketone is acetone.

5. The process of claim 1 further comprising:

(e) reconverting said precipitated calcium-isoflavone complexes to form a product comprising free isoflavone glycosides.

6. The process of claim 5 further comprising repeating steps (a)–(e) using the free isoflavone glycosides from step (e) as the material containing a mixture of isoflavones in step (a) to increase the genistin content of said product.

7. The process of claim 5 wherein said product has a genistin content of at least about 80%.

8. The process of claim 6 wherein said product has a genistin content of at least about 90%.

9. The process of claim 5 wherein said product comprises genistin and daidzin wherein the ratio of genistin to daidzin is at least about 20:1 by weight.

10. The process of claim 9 wherein the ratio of genistin to daidzin is at least about 90:1.

11. The process of claim 5 further comprising:

(f) converting said free isoflavone glycosides to aglycones.

12. The process of claim 11 wherein step (f) comprises acidic or enzymatic hydrolysis.

13. A process for enriching the proportion of genistin in soy isoflavone concentrates, comprising:

(a) extracting a soy isoflavone concentrate with an aqueous organic solvent solution, said soy isoflavone concentrate comprising genistin and daidzin present in said concentrate at an initial weight ratio of genistin to daidzin present in the starting soy isoflavone concentrate;

(b) contacting said extract with calcium oxide or calcium hydroxide thereby forming complexes between calcium and said isoflavones; and (c) removing precipitated calcium-isoflavone complexes from the extract,wherein said precipitated calcium-isoflavone complexes contain calcium-genistin and calcium-daidzin complexes at a weight ratio of at least about 20 times, the initial weight ratio of genistin to daidzin.

14. The process of claim 13 wherein the organic solvent solution is a solution containing an alcohol of low molecular weight, a ketone or a combination thereof.

15. The process of claim 14 wherein the ketone is acetone.

16. The process of claim 13 further comprising:

(d) reconverting said precipitated calcium-isoflavone complexes to form a product comprising free isoflavone glycosides.

17. The process of claim 16 further comprising repeating steps (a)–(d) using the free isoflavone glycosides from step (d) as the soy isoflavone concentrate in step (a) to increase the genistin content of said product.

18. The process of claim 17 wherein said product has a genistin content of at least about 80%.

19. The process of claim 16 wherein said product comprises genistin and daidzin wherein the ratio of genistin to daidzin is at least about 50 times, the initial weight ratio of genistin to daidzin.

20. The process of claim 16 further comprising:

(e) converting said free isoflavone glycosides to aglycones.

21. The process of claim 20 wherein step (e) comprises acidic or enzymatic hydrolysis.

22. A composition comprising a genistin enriched product produced in accordance with the process of claim 16.

* * * * *